United States Patent
Huter et al.

(10) Patent No.: US 6,511,496 B1
(45) Date of Patent: Jan. 28, 2003

(54) EMBOLIC PROTECTION DEVICE FOR USE IN INTERVENTIONAL PROCEDURES

(75) Inventors: Benjamin C. Huter, Murrieta, CA (US); Scott J. Huter, Temecula, CA (US); Christopher L. Steadham, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 229 days.

(21) Appl. No.: 09/659,949

(22) Filed: Sep. 12, 2000

(51) Int. Cl.[7] .............................................. A61M 29/00
(52) U.S. Cl. ........................................................ 606/200
(58) Field of Search ................................ 606/191, 192, 606/194, 200

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Hewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |

(List continued on next page.)

FOREIGN PATENT DOCUMENTS

| | | |
|---|---|---|
| EP | 0 472 334 A1 | 2/1992 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO 00/49970 | 8/2000 |

*Primary Examiner*—John J. Calvert
*Assistant Examiner*—Shaun R Hurley
(74) *Attorney, Agent, or Firm*—Fulwider Patton Lee & Utecht, LLP (57) ABSTRACT

An intravascular filter device for capturing embolic particles entrained in blood flowing in an arterial vessel during an interventional procedure. The filter includes an expandable strut assembly and a filtering medium. Each strut is coated with an elastic polymer in order to minimize trauma to an arterial lumen upon deployment of the filter and to ensure secure adhesion of the filtering medium to the struts. Attached to the coating of the strut assembly is the filtering medium which is formed from a thin elastic polymer membrane containing a plurality of holes which allow blood to pass through filter while capturing embolic particles. The filtering medium is attached to the layer of polymeric material by laser welding, ultrasonic welding or adhesive bonding.

30 Claims, 4 Drawing Sheets

U.S. PATENT DOCUMENTS

| | | |
|---|---|---|
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,836,969 A * | 11/1998 | Kim et al. ............ 606/200 |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,928,260 A * | 7/1999 | Chin et al. ............ 606/200 |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A * | 12/1999 | Daniel et al. ............ 606/200 |
| 6,013,093 A | 1/2000 | Nott et al. |
| 6,152,946 A | 11/2000 | Broome et al. |
| 6,171,327 B1 | 1/2001 | Daniel et al. |
| 6,179,859 B1 | 1/2001 | Bates et al. |

\* cited by examiner

EMBOLIC PROTECTION DEVICE FOR USE IN INTERVENTIONAL PROCEDURES

BACKGROUND OF THE INVENTION

The present invention relates generally to the field of percutaneous transluminal treatment of stenosed or narrowed arteries in the human vascular system. More particularly, the invention is directed to an embolic protection device for capturing particles dislodged from a stenosis during an interventional procedure performed to improve blood flow through the stenosed artery.

Arteries can become stenotic in a number of ways. Often, a stenosis or lesion forms due to an accumulation of atherosclerotic plaque on the walls of a blood vessel. Atherosclerotic plaque is typically a hard calcified substance, particles of which tend to dislodge during interventional procedures and flow freely in the circulatory system. A stenosis also may form from an accumulation of thrombus material which is typically softer than atherosclerotic plaque, but can nonetheless cause restricted blood flow in the lumen of a vessel. Like atherosclerotic plaque, thrombus material also tends to dislodge during interventional procedures. As used here, the term emboli refers to free flowing particulates whether composed of plaque or thrombus material. Such free flowing emboli are dangerous since they may become lodged in a small blood vessel and occlude or partially occlude the vessel.

Various approaches have been developed to treat a stenotic lesion in the vasculature. Among the most common are balloon angioplasty, laser angioplasty, and atherectomy. Balloon angioplasty is directed towards relieving the constriction in the artery by radially expanding the stenosis against the artery wall, while laser angioplasty and atherectomy attempt to remove the stenosis from the artery.

In a typical balloon angioplasty procedure, a guiding catheter is percutaneously introduced into the cardiovascular system of a patient through the femoral artery by means of a conventional Seldinger technique and advanced within a patient's vascular system until the distal end of the guiding catheter is positioned at a point proximal to the lesion site. A guide wire and a dilatation catheter having a balloon on the distal end are introduced through the guiding catheter with the guide wire sliding within the dilatation catheter. The guide wire is first advanced out of the guiding catheter into the patient's vasculature and is directed across the arterial lesion. The dilatation catheter is subsequently advanced over the previously advanced guide wire until the dilatation balloon is properly positioned across the lesion. Once in position, the expandable balloon is inflated to a predetermined size with a radiopaque liquid at relatively high pressures to radially compress the atherosclerotic plaque of the lesion and expand the lumen of the artery. The balloon is then deflated to a small profile so that the dilatation catheter may be withdrawn from the patient's vasculature. Blood flow is then resumed through the dilated artery. As should be appreciated by those skilled in the art, while the above-described procedure is typical, it is not the only method used in angioplasty.

The procedures for laser angioplasty and atherectomy are similar to that of balloon angioplasty in that a guiding catheter is introduced into the patient's vasculature through a conventional Seldinger technique and a guide wire is typically advanced through the guiding catheter and across an arterial lesion to a point distal of the lesion. However, in laser angioplasty, a high intensity laser is used to ablate the lesion by superheating and vaporizing the stenotic matter rather than expanding the lesion with a balloon. In atherectomy, a specialized catheter containing rotating cutting blades is used to mechanically cut or abrade the stenosis from the artery wall.

With all of the above procedures, the treated artery wall suffers a degree of trauma and in a small percentage of cases may abruptly collapse or may slowly narrow over a period of time. To prevent either of these conditions, the treatment procedure may be supplemented by implanting within the arterial lumen a prosthetic device known as a stent. A stent is a small tubular metallic structure which is fitted over a catheter balloon and expanded at the lesion site. Stents serve to hold open a weakened blood vessel and prevent the blood vessel from narrowing over time.

Balloon angioplasty, laser angioplasty, atherectomy, and stenting procedures have proven successful and are widely used in the treatment of stenosis of the coronary arteries and have, for many patients, eliminated the need for invasive bypass surgery. However, all of the above procedures tend to create embolic particles which in certain critical arteries, such as the carotid arteries, can create a significant risk of ischemic stroke. For this reason, these beneficial techniques have not been widely used in treating the carotid arteries.

Embolic particles may be created during an angioplasty procedure since stenoses formed from hard calcified plaque tend to crack upon radial expansion. Upon cracking, emboli will be released into a patient's bloodstream. Emboli may be formed during a stent placement procedure as well when the lesion is cracked since the metal struts of the stent may cut into the stenosis shearing off plaque or thrombus material. In laser angioplasty, complete vaporization of the stenosis is the intended goal of the procedure. In practice however, not all particles from the stenosis are vaporized during the laser ablation process and thus some particles enter the bloodstream. During an atherectomy procedure, a constant stream of particles is cut from the stenosis. Typically a suction catheter is used to capture these particles. However, it is often necessary to pull a high vacuum in order to remove all debris created by the cutting process. In some circumstances, it is not possible to pull a high enough vacuum to remove all debris without causing radial collapse of the weakened artery. Thus, some particles will not be drawn into the suction catheter and will flow downstream as emboli.

Numerous embolic filters or traps for deployment distal of a lesion site have been proposed. Some of these devices use a form of woven wire mesh basket to capture emboli. A typical example of the wire mesh basket type of intravascular filter is described in U.S. Pat. No. 4,873,978, entitled "Device and Method for Emboli Retrieval" issued to Ginsburg. Ginsburg discloses a removable vascular filter permanently attached to a guide wire for deployment from a catheter. The filter is comprised of an expandable wire mesh basket employing diamond shaped cells. Upon deployment, the filter expands to contact the walls of the lumen, thereby straining emboli found in the blood flow of the lumen.

A variation of the wire mesh basket approach is described in U.S. Pat. No. 5,152,777, entitled "Device and Method for Providing Protection From Emboli and Preventing Occlusion of Blood Vessels" issued to Goldberg et al. This device consists of a filter having of a plurality of resilient, stainless steel wire arms joined at one end so as to form a conical surface and having rounded tips at their other ends to prevent damage to the vessel walls. Each arm is wound with wire in a form similar to a coil spring. Goldberg proposes that emboli entrained in blood flowing past the spring arms will be caught in the coils of the arms.

Prior art wire mesh filters have several drawbacks. The most significant of which is the relatively large cell size of the mesh. Embolic particles with nominal diameters smaller than 150 microns can still pose a serious risk of occluding or partially occluding fine vasculature. A very fine wire mesh basket may have cells with openings as large as 3000–4000 microns. Thus, wire mesh filters may not be able to trap small embolic particles and therefore may be unsuitable during the treatment of lesions in the carotid arteries where any emboli produced by an interventional procedure have a short flow path to the fine vasculature of the brain.

Other devices for capturing emboli in blood flowing in a patient's vasculature have been developed which utilize filtering elements having microporous membranes capable of filtering much smaller embolic particles. These embolic protection devices utilize a filtering medium which is more flexible than metal mesh and can be bonded to a deployment mechanism that opens and closes the filter element within the artery. The filter material is usually adhesively attached to the deployment mechanism, which is usually made from stainless steel, nickel titanium alloy, or other suitable metallic materials. The filter material can be appropriately shaped to create a "basket" to capture embolic material which forms when the deployment mechanism is actuated in the artery. The attachment of the filter material to the deployment mechanism must be sufficiently strong to prevent the filter material from becoming detached during usage. In the event that the bond between the filter element and deployment mechanism is weakened, there is a possibility that the "basket" will not fully deploy or will improperly sit within the patient's vasculature. Such an event can result in a serious risk that not all of the embolic particles created during the interventional procedure will be captured by the filtering device.

What is needed, therefore, is a reliable filtering device that may be placed distal of an arterial lesion and used in conjunction with balloon angioplasty, laser angioplasty, atherectomy, stenting, or other interventional procedures. The device should be able to reliably trap embolic debris and thereby render the above named procedures safe for treating lesions in the carotid arteries. Further, the device should be relatively easy to deploy and remove from the patient's vasculature. The present invention meets these and other needs.

SUMMARY OF THE INVENTION

The present invention provides an improved intravascular filter device for capturing embolic particles entrained in blood flowing in an arterial vessel during an interventional procedure. The filter device is intended to be used as a primary filter in conjunction with interventional treatment procedures such as balloon angioplasty and/or stenting. The filter device may also be used as a secondary filter in conjunction with a suction catheter in atherectomy and laser angioplasty procedures. The filter device is capable of capturing small embolic particles, thereby dramatically increasing the safety of balloon angioplasty and stenting in critical arteries. As a result, balloon angioplasty and stenting procedures may be more frequently used in arteries, such as the carotid arteries, where the risk of stroke from embolic particles is exceptionally high.

The filter device of the present invention includes an expandable strut assembly and a filtering element. The strut assembly is compressible to an initial low profile delivery diameter and is expandable to a larger deployed diameter. The strut assembly is composed of a plurality of struts which may be made from, for example, spring steel, shape memory alloys or polymers. The struts are coated with an elastic polymer in order to minimize trauma to an arterial lumen upon deployment of the filter device and to ensure a strong bond to the filtering element. The filtering element is attached directly to the polymer coated strut assembly. The filtering element is formed from a thin elastic polymer membrane containing a plurality of laser drilled holes. The laser drilling process allows for holes in the order of about 25 to 200 microns or larger to be drilled in the filter membrane. Thus, if necessary, extremely fine embolic particles may be captured with a device made in accordance with the present invention.

The layer of polymeric material which coats the struts of the strut assembly provides a medium by which an extremely strong bond can be made to the filtering element, while providing a softer elastic surface to minimize trauma to the arterial wall once the filter device is deployed in the artery. The polymeric material may be any suitable biocompatible material which will adhere to the metallic strut, such as polyurethane. Other materials include polyester, polyamide, polyethylene, polytetrafluorothylene ("PTFE"), expanded polytetrafluoroethylene ("ePTFE"), FEP, EAA copolymer and polyolefin. The polymeric coating material should be thermally compatible with the filtering element and may be applied to the strut and strut assembly using known methods, such as dip coating, spraying and electrodeposition. The filtering element may be attached to the strut assembly utilizing laser welding, ultrasonic welding, solvent bonding, or adhesive bonding. Where the filtering element and polymeric coating material are both of the same class of polymer, laser welding provides a particularly strong bond between the coated strut and membrane filter. When the filter element and polymeric coating material are dissimilar, adhesive bonding provides a suitably strong bond between the two elements.

The filter device may be delivered to a desired location within an artery by means of a guide wire and a delivery sheath. The filter device can be rotatably attached to the guide wire by a proximal collar of the strut assembly. A distal collar of the strut assembly can slide axially over the guide wire and is also rotatable on the guide wire as well. This allows the strut assembly to move between its collapsed and expanded positions while still allowing the filter to freely rotate or "spin" about the guide wire. The attachment of the proximal collar of the strut assembly to the guide wire allows the restraining sheath to be retracted from the filter and permits a recovery sheath to be placed over the expanded strut assembly to move the strut assembly back to the collapsed position when the embolic protection device is to be removed from the patient's vasculature.

Other features and advantages of the present invention will become more apparent from the following detailed description of the invention, when taken in conjunction with the accompanying exemplary drawings.

DETAILED DESCRIPTION OF THE PREFERRED EMBODIMENTS

The filter device of the present invention described below is shown as used in conjunction with a balloon angioplasty procedure. However, the filter device is not intended to be limited only to use with balloon angioplasty procedures, rather, the filter device may be used in any interventional procedure where it is important to trap and remove fine particles of embolic debris.

Figure 1:
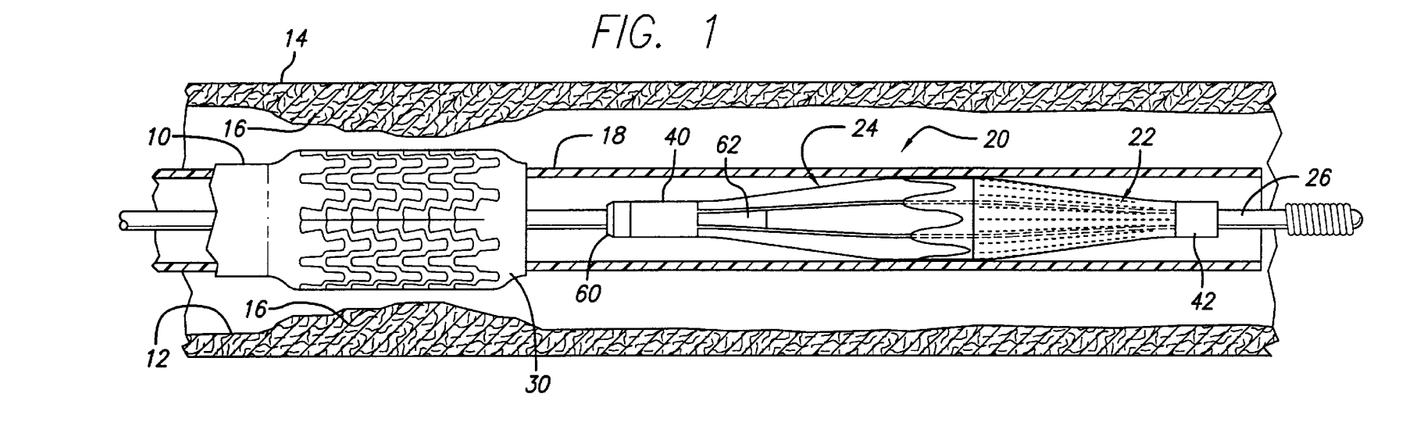
FIG. 1 is an elevational view, partially in cross section, of an embolic protection device embodying features of the present invention showing the filtering element and strut assembly in the collapsed position and positioned within a restraining sheath and disposed within a body vessel.

Referring now to FIG. 1, a guiding catheter 10 has been percutaneously introduced into a patient's vascular system by means of a conventional Seldinger technique and advanced through a lumen 12 of an arterial vessel 14 to a position proximal of an arterial lesion 16. A delivery sheath 18 can be back- loaded on an emboli filter device 20 made in accordance with the present invention. The filter device 20 is shown in its collapsed or low profile position. The filter device 20 includes a filtering element 22 and an expandable strut assembly 24. The filter device 20 is rotatably mounted on the distal end of the guide wire 26. The guide wire 26 has been advanced to a point where the filter device 20 is positioned distal of the arterial lesion 16. Upon positioning the filter device 20 distal to the lesion 16, the delivery sheath 18 is retracted, thereby deploying the filter device 20 within the lumen 12 of the arterial vessel 14. The deployed filter device 20 is depicted in FIG. 2.

Figure 2:
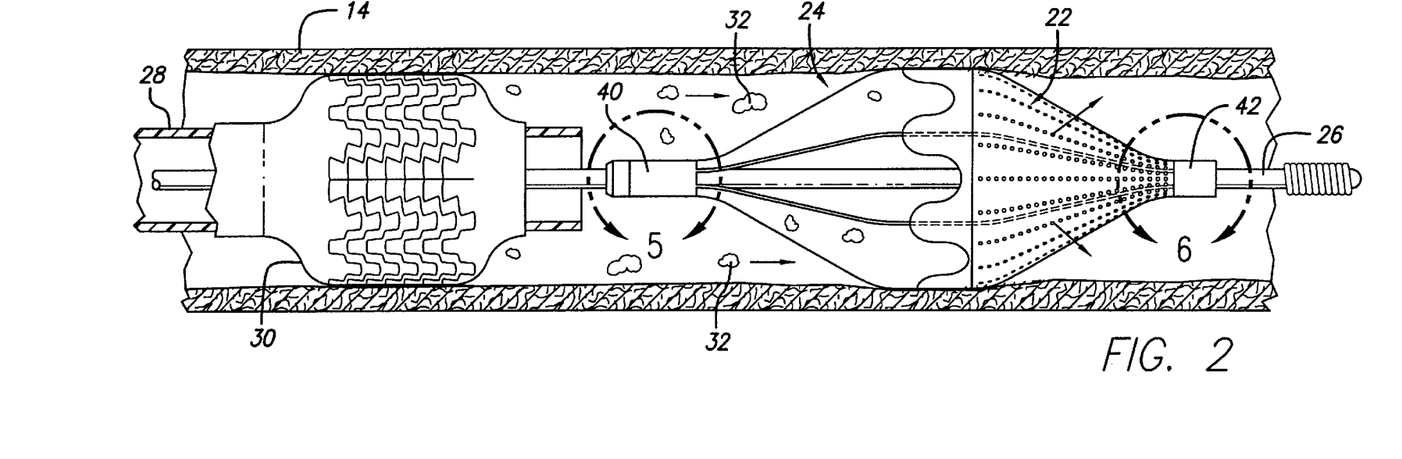
FIG. 2 is an elevational view, partially in cross section, similar to that shown in FIG. 1, wherein the filtering element and strut assembly are in the expanded position within the vessel.

Referring now to FIG. 2, subsequent to deployment, the delivery sheath 18 is withdrawn from the guiding catheter 10 and a balloon dilitation catheter 28 having an expandable member, here shown as an inflation balloon 30, is advanced over the guide wire 26 to a position across the lesion 16. Once in position across the lesion 16, the balloon 30 is expanded with radiopaque fluid at high pressure, thereby radially expanding or dilating the arterial lesion 16. Upon dilation, the hard calcified atherosclerotic plaque which forms the lesion may crack and form embolic particles or emboli 32. The emboli 32 flowing downstream of the dilated lesion 16 are captured by the filtering element 22 of the filter device 20. Once the angioplasty procedure is complete, the balloon catheter 28 is removed and may, as determined by the treating physician, be followed by a stent-delivery catheter (not shown) for placement of a stent across the dilated lesion. The stent placement procedure may also form embolic particles 32 which would be captured by the filter device 20. Once the angioplasty and/or stenting procedure is completed, a retraction sheath (not shown) is introduced into the guiding catheter 10 and advanced to a point distal of the lesion 16 and proximal of the filter device 20. The filter device 20 is subsequently withdrawn into the retraction sheath and the sheath, filter, guide wire, and embolic debris captured by the filter device are withdrawn from the patient.

Figure 3:
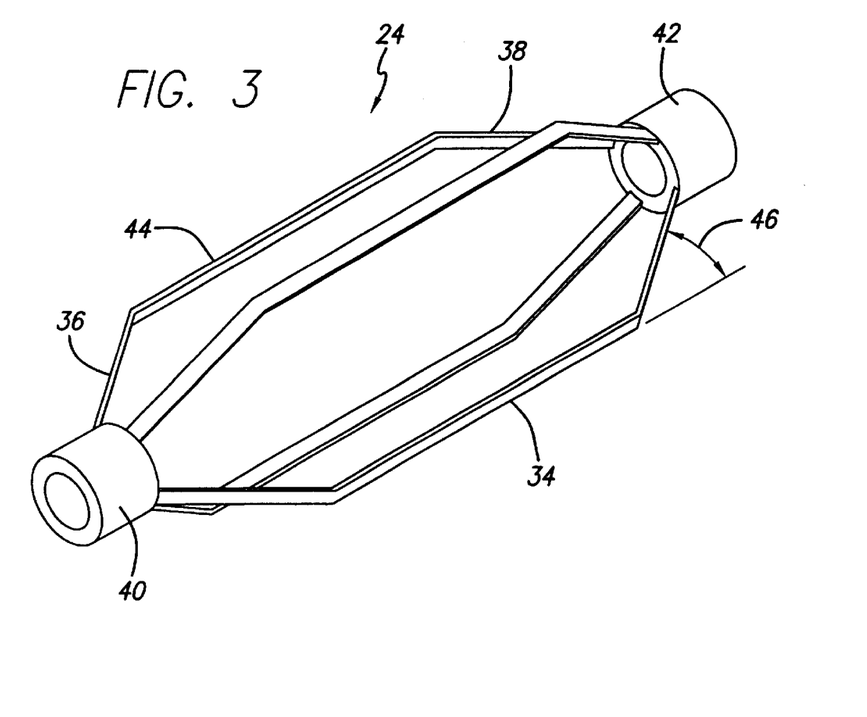
FIG. 3 is a perspective view of the strut assembly which forms part of the filter device of the present invention as shown in its expanded position.

Referring now to FIGS. 1–4, the expandable strut assembly 24 of the filter device 20 possesses spring-like or self-expanding properties and can move from a compressed or collapsed position as shown in FIG. 1 to an expanded or deployed position shown in FIG. 2. With particular reference to FIG. 3, the strut assembly 24 includes an elongated cylindrical center portion 34 and proximal and distal end portions 36 and 38 which are shaped as truncated cones, terminating at proximal and distal, hollow, cylindrical, guide wire collars 40 and 42. Starting from the proximal collar 40, the strut assembly 24 comprises a plurality of individual struts 44 which taper upward to form the proximal truncated cone portion 36 of the of the strut assembly 24. The struts 44 continue, extending longitudinally, to form the elongated, straight, center portion 34 of the strut assembly. The struts 44 then taper downward forming the distal truncated cone portion 38 of the strut assembly and terminate at the distal collar 42. Arrows 46 in FIG. 3 show the angle that the distal truncated cone portion 38 makes with the center portion 34. While the figures show only four individual struts, the invention is not limited to this configuration as strut assemblies containing more or less struts are practical.

The strut assembly 24 may be produced by several methods including electro-discharge machining and chemical etching. One method is to laser machine a thin-walled tubular member, such as a hypotube. In this procedure, a computer controlled laser cuts away portions of the hypotube following a pre-programmed template to form the desired strut pattern. Methods and equipment for laser machining small diameter tubing may be found in U.S. Pat. Nos. 5,759,192 (Saunders) and 5,780,807 (Saunders), which have been assigned to Advanced Cardiovascular Systems, Inc.

The tubing used to make the strut assembly may be made of any biocompatible spring steel or shape memory alloy. The 300 series stainless steel alloys are well suited to this application as is type 316L stainless steel per ASTM F138-92 or ASTM F139-92 grade 2. Of the shape memory or super-elastic alloys, Nitinol or a 55% nickel −45% titanium alloy are suitable materials. Other shape memory alloys such as Ni-Ti-X (X being V, Co, Cu, Fe) ternary alloys, Cu-Al-Ni ternary alloys and Cu-Zn-Al ternary alloys are also suitable. It should be appreciated that although the strut assembly 24 has been described herein as a self-expanding assembly, the method for attaching the filtering element to the struts and strut assembly can also be performed on filtering devices which are not necessarily self-expanding. For example, if the strut assembly requires the application of force to deploy the struts between a collapsed and expanded position, rather than using self-expanding components, it is still possible to coat the strut assembly with a polymeric material and attach the filtering element in the same manner as described herein. Thus, the manner of coating the struts and strut assembly with a polymeric material to create a softer surface to reduce possible trauma to the vessel wall and to achieve a strong bond between strut assembly and filtering element can be broadly applied to numerous filtering devices which use expandable struts as a means for deploying a filter.

Typically, suitably sized tubing for making the strut assembly 24 will have an outer diameter on the order of about 0.020–0.040 inches, with a wall thickness of about 0.003–0.006 inches. However, tubing size will vary depending upon the application. The strut assembly may be machined from seamless tubing. However, tubing formed by rolling flat, sheet stock into a cylinder with welded longitudinal edges is also suitable as is rolled sheet stock which has been drawn through a circular die.

Figure 4:
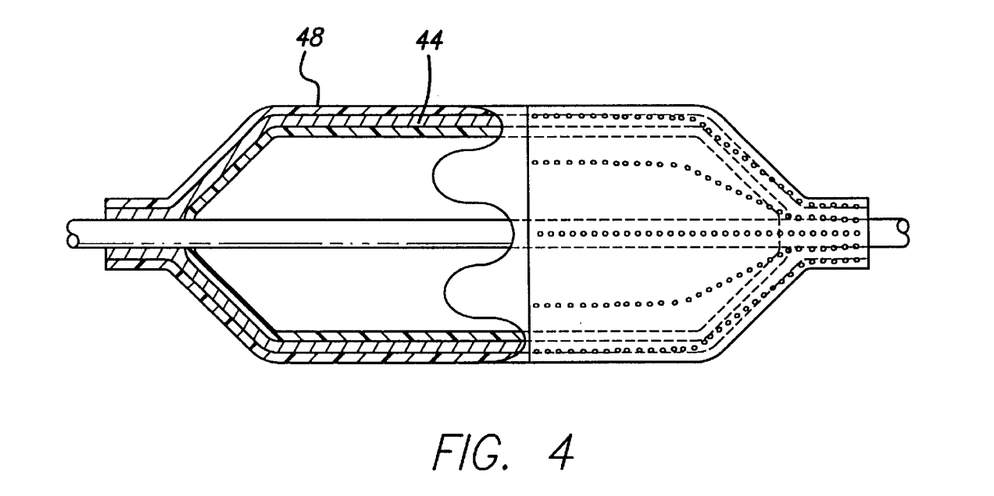
FIG. 4 is a sectional view, partially fragmented, of the expandable strut assembly and filtering element which form one embodiment of the present invention.

With particular reference to FIG. 4, each strut of the strut assembly 24 is coated with a layer 48 of polymeric material. The layer 48 serves to provide an interface by which the membrane filter element 22 may be securely attached to the struts 44. The polymeric material may be any suitable bio-compatible material which will adhere to the metallic strut assembly 24. Polyurethane is one such material. Other materials such as polyester, polyamide, polyethylene, polytetrafluoroethylene ("PTFE"), expanded polytetrafluoroethylene ("ePTFE"), FEP, EAA copolymer and polyolefin are also suitable. The polymeric layer 48 may be applied to the strut assembly 24 using known bonding method, examples of which are dip coating, spraying, and electro-deposition.

The layer 48 of polymeric material can be disposed on the outer surface of the strut and strut assembly in order to provide a protective coating which minimizes trauma to the wall of the arteries and which provides a strong bonding surface for affixing the filtering element to the struts. The layer 48 of polymeric material can first be applied to the tubing used to make the strut assembly and the entire coated tubing could be cut to the particular strut pattern utilizing a computer controlled laser or other means described above. Alternatively, the tubing could be first cut to make the strut assembly and thereafter the layer 48 of polymeric material could be applied to the strut assembly. It is sufficient that the layer 48 is applied to the external surface of the strut assembly when the filtering element 22 is placed on the outside of the strut assembly. In the event that the filtering element 22 is placed on the inside of the strut assembly, then the inside surface of the strut assembly would also have to be coated.

The filtering element 22 may be formed as an integral unit by molding processes known to those skilled in the art or the membrane may be composed of several cut sheets each of which is individually attached between adjacent struts 44 of the strut assembly 24. The filtering element 22, whether formed as an integral unit or from individual sheets, may be placed either on the outside or the inside of the strut assembly 24. In the embodiment shown in the drawings, the filtering element 22 is placed on the outside of the strut assembly 24 as this placement is believed to inflict less trauma on the lumen wall of the arterial vessel when the filter is deployed.

One suitable material which can be used for the filtering element 22 is polyurethane film of about 0.001 to about 0.005 inch thickness. Many other bio-compatible polymers such as polyester, polyamide, polyethylene, PTFE, expanded-PTFE, and polyolefin are also suitable.

The filtering element 22 may be attached to the strut assembly 24 by known methods such as laser welding, ultrasonic welding, and adhesive bonding. Where the filtering element 22 and the material which encapsulates the struts 44 are both of the same class of polymer, for instance, a thermoplastic form of polyurethane, laser welding is particularly suitable. Laser welding of similar materials produces a particularly strong joint and methods of laser welding are known to those skilled in the art. For example, a spot, tack or pulse weld can be used to weld the filtering element to the strut assembly. The welds can be placed either on the inside surface of the filtering element or on its exterior surface. Where the filtering element 22 and the coating material are dissimilar, adhesive bonding is a suitable method of attachment. A suitable adhesive may be a thermoplastic adhesive. A thermoplastic fluoropolymer adhesive such as fluorinated ethylene propylene ("FEP") is suitable for use.

Figure 7:
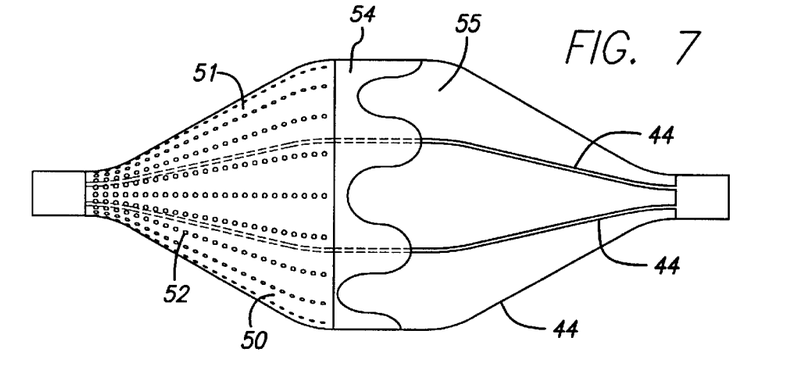
FIG. 7 is an enlarged side view of the filtering element shown in FIGS. 1 and 2.
Figure 8:
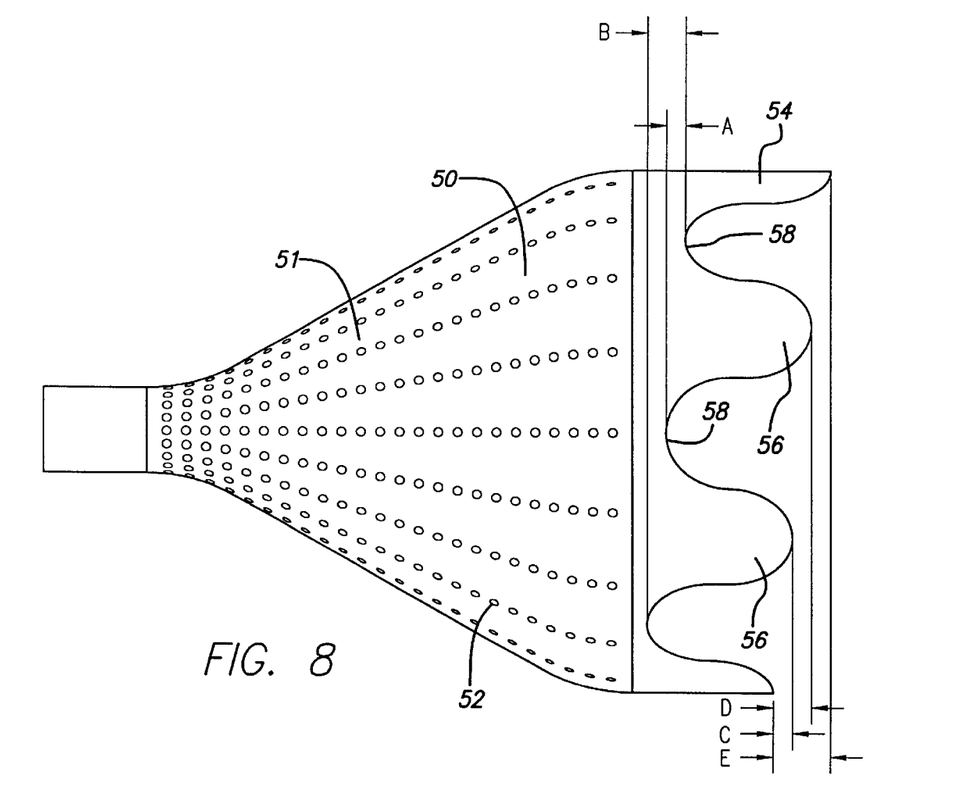
FIG. 8 is an enlarged side view of the filtering element shown in FIGS. 1 and 2.

Referring now to FIGS. 2, 7, and 8, the filtering element 22 includes a leading edge 54, which forms an inlet opening 55, and a central portion 50 formed as a conical basket 51, which includes a plurality of openings or holes 52 for the filtering of emboli. The filtering element 22 is made from a thin membrane of flexible, elastic, polymeric material. The filtering element 22, upon deployment within the vessel lumen 14, expands in a manner similar to a parachute due to the pressure of blood flowing into the basket 51. This parachute like expansion effect causes the leading edge 54 to contact the lumen walls thereby preventing unfiltered blood from leaking around the leading edge 54.

Particle filtering is controlled by the size of the holes 52 in the membrane 22. The holes 52 can be laser drilled through the central portion 50 of the membrane. Laser drilling is capable of producing holes as small as 25 microns in thin membranes. Therefore, if desired, a filter in accordance with the present invention could capture extremely fine embolic debris. Embolic particles smaller than 150 microns generally will not occlude or partially occlude blood vessels branching from the carotid arteries. Thus, hole sizes of about 130 microns could be formed on the filtering element. Other considerations effect the size of the holes 52. Smaller holes may result in reduced blood flow downstream of the filter. Low blood flow could result in a blood starvation condition with adverse effects on the patient. This situation is particularly critical in the carotid arteries where a starvation condition may lead to oxygen deprivation in the patient's brain, a highly undesirable condition. Thus, the filter hole size should be chosen with regard to the intended application. For example, in the coronary arteries where the risk of stroke is lower than in the carotid arteries, it may be desirable to use a hole size larger than 130 microns to improve blood flow through the filter.

The leading edge 54 of the filter element 22 may be straight or in a configuration having a pattern of alternating peaks 56 and valleys 58. This configuration of the filter edge 54 allows the filter to be incrementally introduced into the delivery sheath 18, which allows for a gradual and smooth transition into the sheath and minimizes the possibility of tearing the filtering element 22. The edge configuration also tends to reduce the stress concentration in the valley regions 58. Preferably, the peaks 56 of the filtering element 22 are aligned with the struts 44 of the strut assembly 24, as shown in FIG. 7. Thus, the number of peaks 56 may vary with the number of struts 44 on the strut assembly 24. For example, as shown by dimensions A through E in FIG. 8, each peak 56 and valley 58 may be either higher or lower than adjacent peaks and valleys.

Referring now to FIGS. 1–6, the filter device 20 is shown rotatably secured to a shaft member such as the guide wire 26. The filter device 20 is slid onto the guide wire 26 with the guide wire sliding within the proximal and distal collars 40 and 42. The proximal collar 40 of the expandable strut assembly 24 is mounted between a tapered fitting 60 located proximal of the collar 40 and a radiopaque marker band 62 located distal of the collar 40. The tapered end fitting 60 and marker band 62 fix the proximal collar 40 onto the guide wire 26 to prevent any longitudinal motion of the proximal collar along the guide wire but allow for rotation of the proximal collar 40 and of the filter device 20 about the guide wire. This particular construction allows the expandable strut assembly 24 to rotate or "spin" freely about the guide wire 26 while allowing the strut assembly to move longitudinally along the guide wire at the distal collar 42. The above example is merely illustrative of one method of rotatably attaching the filter 20 to the guide wire. Other ways of performing this same function can be employed with the present invention.

Figure 5:
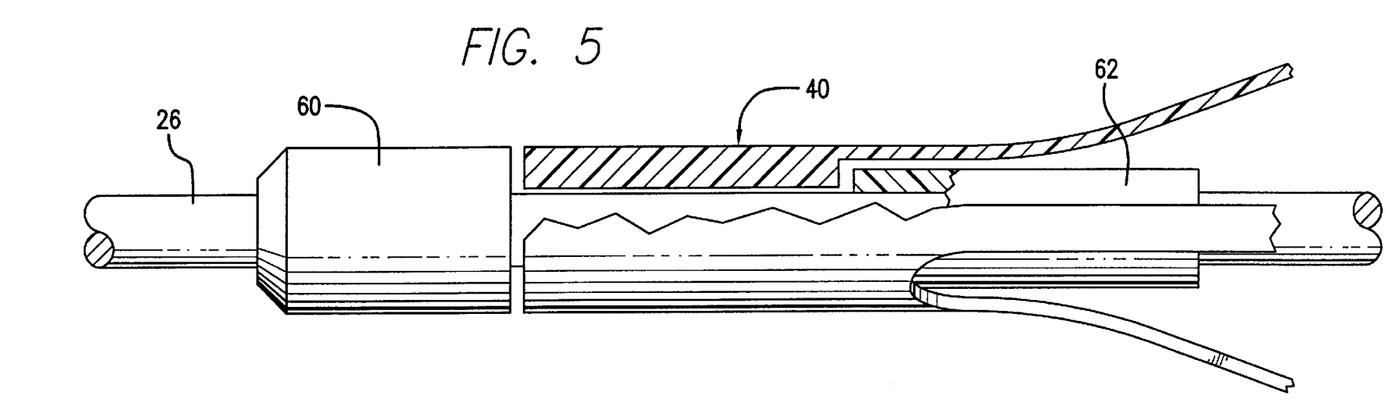
FIG. 5 is an elevational view, partially in cross section, of the proximal end of the expandable strut assembly of FIG. 2 as it is rotatably attached to the guide wire.
Figure 6:
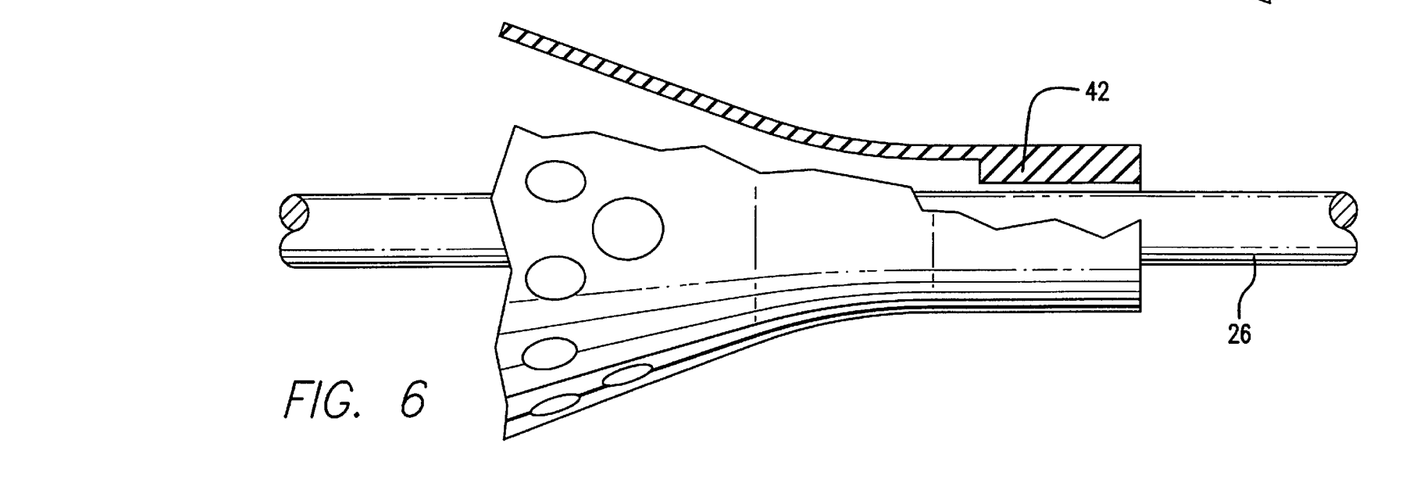
FIG. 6 is an elevational view, partially in section and fragmented, showing the distal end of the filtering device of FIG. 2 as it is slidably mounted on a guide wire.

By rotatably mounting the filter device 20 to the guide wire in the manner described, the filter device 20 will lengthen longitudinally with the distal collar 42 sliding along the guide wire 26 when the strut assembly 24 is compressed for insertion into the delivery sheath 18. Likewise, the filter will contract longitudinally while its expands radially upon release from the delivery sheath 18 and deployment within the vessel lumen 12. An advantage of rotatably mounting the filter on the guide wire is that the filter will remain stationary should the guide wire 26 be rotated at its proximal end after the filter 20 has been deployed within the patient's vasculature. If the filter were to rotate after deployment, the seal of the leading edge 54 of the filtering element 22 against the lumen wall would be disturbed possibly allowing unfiltered blood to bypass the filter. Additionally, rotation of the filter device 20 within the artery could cause some trauma to the wall of the artery.

With reference to FIGS. 1 and 2, after the filter device 20 has been attached to the guide wire 26, the filter may be prepared for use by simply backloading the guide wire 26 into the delivery sheath 18 and subsequently compressing and back-loading the filter 20 into the sheath. The filter device 20 may be front-loaded into the sheath, however, the delivery sheath is typically about 135 cm long and forcing the filter device to travel the full length of the sheath may tear or otherwise damage the filtering element 22. Thus, back-loading is recommended. After loading, the delivery sheath 18 is advanced through the pre-positioned guiding catheter 10 to a point distal of lesion 16. The filter device 20 is deployed simply by retracting the delivery sheath. After deployment from the sheath, the spring-like strut assembly 24 expands against the lumen wall 12 and blood flowing within the lumen inflates the filter element 22 causing the leading edge 54 of the filter element 22 to seal against the lumen wall 12. At this point, the filter is fully functional and the desired interventional procedure may be performed.

After the interventional procedure is completed and any associated equipment removed, the filter device 20 may be withdrawn as follows. A recovery sheath (not shown) is advanced through the guiding catheter 10 to a point just proximal of the filter 20. Generally, this recovery sheath has a slightly larger inner diameter than the delivery sheath 18 since the struts 44 are now deployed and the recovery sheath may require increased hoop strength at its distal end to properly move the strut assembly 24 back into its collapsed position. The collapse of the expandable strut assembly 24 can be accomplished by holding the guide wire 26 and moving the proximal end of the recovery sheath forward which will move the distal end of the sheath over the struts 44. Alternatively, the recovery sheath can be held stationary while the proximal end of the guide wire 26 is retracted backward to pull the filter device 20 into the recovery sheath. Upon collapse of the filter device 20, any embolic debris generated and entering the bloodstream during the interventional procedure will remain trapped inside the filtering element 22 and will be withdrawn from the bloodstream when the filter device 20 is removed from the patient's vasculature.

It will be appreciated that a new intravascular filter for capturing embolic particles formed during an angioplasty or other interventional procedure has been presented. The filter device is capable of capturing fine embolic particles, thereby improving the safety of these procedures particularly when they are employed in critical arteries such as the carotid arteries. While specific embodiments have been described in detail, as will be apparent to those skilled in the art, modifications and improvements may be made to the device and method disclosed herein without departing from the scope of the invention. Accordingly, it is not intended that the invention be limited, except as by the appended claims.

What is claimed is:

1. A filter device for capturing embolic particles released into a vessel lumen of a patient, comprising:
   an expandable strut assembly having a plurality of expandable struts adapted to move between a collapsed position and an expanded position;
   a layer of polymeric material disposed on the expandable struts; and
   a filtering element attached to the polymeric layer disposed on the struts which is movable with the struts to expand and contact the wall of the vessel lumen, wherein embolic debris entrained in the fluid flow of the vessel is captured by the filtering element as fluid flows through the filtering element.

2. The filter device of claim 1, wherein:
   the expandable struts are self-expanding.

3. The filter device of claim 1, wherein:
   the layer of polymeric material disposed on the expandable struts is selected from the group consisting of polyester, polyamide, polyethylene, polytetrafluoroethylene ("PTFE"), expanded polytetrafluoroethylene ("ePTFE"), polyurethane, FEP, EAA copolymer and polyolefin.

4. The filter device of claim 1, further including:
   a shaft member having proximal and distal ends; and
   wherein the expandable strut assembly is rotatably affixed to the shaft member.

5. The filter device of claim 1, wherein:
   the filtering element is a thin elastic membrane.

6. The filter device of claim 5, wherein:
   the elastic membrane has a thickness within the range of about 0.001 inches to about 0.005 inches.

7. The filter device of claim 5, wherein:
   the elastic membrane is made from a material selected from the group consisting of polyurethane, polytetrafluoroethylene ("PTFE"), expanded polytetrafluoroethylene ("ePTFE"), polyamide, polyolefin, and polyethylene.

8. The filter device of claim 7, wherein:
   the layer of polymeric material disposed on the expandable struts is selected from the group consisting of polyester, polyamide, polyethylene, polytetrafluoroethylene ("PTFE"), expanded polytetrafluoroethylene ("ePTFE"), FEP, polyurethane, EAA copolymer, and polyolefin.

9. The filter device of claim 1, wherein:
   the layer of polymeric material is made from the same material which forms the filtering element.

10. The filter device of claim 1, wherein:
    the layer of polymeric material is the same class of polymer as the material which forms the filtering element.

11. The filtering device of claim 10, wherein:
    the filtering element and the layer of polymeric material disposed on the expandable struts are made from polyurethane.

12. The filtering device of claim 1, wherein:
    the filtering element is bonded to the layer of polymeric material by laser welding.

13. The filter device of claim 1, wherein:
the filtering element is bonded to the layer of polymeric element by ultrasonic welding.

14. The filtering device of claim 1, wherein:
the filtering element is bonded to the layer of polymeric material by adhesive bonding.

15. The filtering device of claim 14, wherein:
the adhesive is a plastic adhesive.

16. The filtering device of claim 1, wherein:
the filtering element is bonded to the layer of polymer material by solvent bonding.

17. The filtering device of claim 1, wherein:
the strut assembly is made from stainless steel.

18. The filtering device of claim 1, wherein:
the strut assembly is made from nickel-titanium alloy.

19. The filtering device of claim 1, wherein:
the layer of polymeric material encapsulates the expandable struts of the strut assembly.

20. The filtering device of claim 1, wherein:
the layer of polymeric material encapsulates the entire outer surface of the strut assembly.

21. The filter device of claim 1, wherein:
the filtering element includes a leading edge having a pattern of alternating peak and valley regions which prevent the leading edge from entering into a restraining sheath all at one time.

22. The filter device of claim 21, wherein:
the peak portions are attachable to the struts of the expandable strut assembly.

23. The filter device of claim 21, wherein:
the depth of the valley region on the filter edge is a progressively larger dimension from an adjoining valley portion.

24. The filter device of claim 21, wherein:
the depth of the valley portion from the peak portion is the same for each adjacent valley portion.

25. The filter device of claim 21, wherein:
the height of the peak region on the filter edge is a progressively larger dimension from an adjoining peak portion.

26. The filter element of claim 21, wherein:
the height of the peak portion from the valley portion is the same for each adjacent peak portion.

27. The filter device of claim 26, wherein the filtering element is made from a material selected from the group consisting of polyurethane, polytetrafluoroethylene ("PTFE"), expanded polytetrafluoroethylene ("ePTFE"), polyamide, polyolefin, and polyethylene.

28. A filter device for capturing embolic particles released into a vessel lumen of a patient, comprising:
an inner shaft member having proximal and distal ends;
an expandable strut assembly rotatably connected to the inner shaft member having a plurality expandable struts adapted to move between a collapsed position and expanded position;
a layer of polymeric material disposed on the expandable struts; and
a filtering element made from an elastic polymeric material which is attached to the polymeric layer disposed on each strut and is movable with the struts to expand to contact the wall of the vessel lumen, wherein blood is forced to flow through the filtering element to capture embolic debris entrained in the fluid flow of the vessel.

29. The filter device of claim 28, wherein the layer of polymeric material disposed on the expandable struts is selected from the group consisting of polyester, polyamide, polyethylene, polytetrafluoroethylene ("PTFE"), expanded polytetrafluoroethylene ("ePTFE"), FEP, polyurethane, EAA copolymer, and polyolefin.

30. A filter device for capturing embolic particles released into a vessel lumen of a patient, comprising:
a plurality of expandable struts adapted to move between a collapsed position and an expanded position;
means for moving the struts between the collapsed and expanded positions;
a layer of polymeric material disposed on the expandable struts; and
a filtering element attached to the polymeric layer disposed on the struts which is movable with the struts to expand and contact the wall of the vessel lumen, wherein embolic debris entrained in the fluid flow of the vessel is captured by the filtering element as fluid flows through the filtering element.

\* \* \* \* \*